United States Patent
Stahmann

(10) Patent No.: US 11,844,489 B2
(45) Date of Patent: Dec. 19, 2023

(54) RESPIRATORY PHASE DETERMINATION

(71) Applicant: Cardiac Pacemakers, Inc., St. Paul, MN (US)

(72) Inventor: Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 259 days.

(21) Appl. No.: 17/217,217

(22) Filed: Mar. 30, 2021

(65) Prior Publication Data

US 2021/0315479 A1 Oct. 14, 2021

Related U.S. Application Data

(60) Provisional application No. 63/009,304, filed on Apr. 13, 2020.

(51) Int. Cl.
| | | |
|---|---|---|
| *A61B 5/08* | (2006.01) | |
| *A61B 5/021* | (2006.01) | |
| *A61B 5/352* | (2021.01) | |
| *A61B 5/00* | (2006.01) | |
| *A61B 5/113* | (2006.01) | |

(52) U.S. Cl.
CPC ............ *A61B 5/0816* (2013.01); *A61B 5/021* (2013.01); *A61B 5/1135* (2013.01); *A61B 5/352* (2021.01); *A61B 5/4857* (2013.01); *A61B 2562/0219* (2013.01)

(58) Field of Classification Search
CPC . A61B 5/0816; A61B 5/0205; A61B 5/14551; A61B 5/7225; A61B 5/113; A61B 5/021; A61B 2562/0219; A61B 5/1135; A61B 5/7246; A61B 5/7285
See application file for complete search history.

(56) References Cited

U.S. PATENT DOCUMENTS

| 8,626,292 | B2 | 1/2014 | Mccabe et al. |
| 9,403,018 | B2 | 8/2016 | McCabe et al. |
| 2004/0064054 | A1* | 4/2004 | Clift .................. A61B 5/0205 600/483 |
| 2006/0025827 | A1 | 2/2006 | Hatlesad et al. |
| 2008/0119749 | A1 | 5/2008 | Haro et al. |

(Continued)

FOREIGN PATENT DOCUMENTS

WO    WO-2022072280 A1    4/2022

OTHER PUBLICATIONS

"International Application Serial No. PCT/US2021/052212, International Preliminary Report on Patentability dated Apr. 13, 2023", 10 pgs.

(Continued)

*Primary Examiner* — Eric F Winakur
*Assistant Examiner* — Elina Sohyun Ahn
(74) *Attorney, Agent, or Firm* — Schwegman Lundberg & Woessner, P.A.

(57) ABSTRACT

Systems and methods to determine a composite respiration phase of a patient are disclosed, including a signal receiver circuit to receive first and second physiologic information of a patient, and an assessment circuit to determine first respiration phase information of the first physiologic information and to determine the composite respiration phase of the patient using the determined first respiration phase information and the second physiologic information.

19 Claims, 8 Drawing Sheets

(56) References Cited

U.S. PATENT DOCUMENTS

| | | | |
|---|---|---|---|
| 2008/0177156 A1 | 7/2008 | Zhang et al. | |
| 2010/0160992 A1* | 6/2010 | Blomqvist | A61N 1/36557 |
| | | | 607/17 |
| 2013/0172767 A1* | 7/2013 | Dripps | A61B 5/742 |
| | | | 600/529 |
| 2018/0214090 A1* | 8/2018 | Al-Ali | A61B 5/0816 |
| 2022/0095931 A1 | 3/2022 | Stahmann et al. | |

OTHER PUBLICATIONS

"International Application Serial No. PCT/US2021/052212, International Search Report dated Jan. 19, 2022", 4 pgs.
"International Application Serial No. PCT/US2021/052212, Written Opinion dated Jan. 19, 2022", 8 pgs.

* cited by examiner

RESPIRATORY PHASE DETERMINATION

CLAIM OF PRIORITY

This application claims the benefit of priority under 35 U.S.C. § 119(e) of U.S. Provisional Patent Application Ser. No. 63/009,304, filed on Apr. 13, 2020, which is herein incorporated by reference in its entirety.

TECHNICAL FIELD

This document relates generally to detecting patient respiration, and more particularly, but not by way of limitation, to systems and methods for determining a respiratory phase of a patient.

BACKGROUND

Normal patient respiration is automatic, and functions to provide sufficient oxygen ($O_2$) supply to the body and remove carbon dioxide ($CO_2$) to maintain a suitable acid-base status. Medical sensors or devices can detect or monitor respiration, such as to determine one or more respiratory parameters (e.g., respiratory rate, tidal volume, etc.), detect patient respiratory sounds, or to determine periods of patient inspiration or expiration.

Ambulatory medical devices (AMDs) include implantable, subcutaneous, wearable, external, or one or more other type of medical devices having sensors configured to sense physiologic signals from a patient. Detected physiologic signals can be used to determine or monitor patient status or condition. Frequent patient monitoring, such as using one or more AMDs, can enable early detection of worsening patient condition or identification of patients or groups of patients having elevated risk of future adverse events, including hospitalization. Early detection of worsening patient condition can prevent or reduce patient hospitalization. Identifying and safely managing patient risk of worsening condition may reduce patient hospitalizations, the amount or severity of medical interventions, and overall healthcare costs.

SUMMARY

Systems and methods to determine a composite respiration phase of a patient are disclosed, including a signal receiver circuit to receive first and second physiologic information of a patient, and an assessment circuit to determine first respiration phase information of the first physiologic information and to determine the composite respiration phase of the patient using the determined first respiration phase information and the second physiologic information.

An example (e.g., "Example 1") of subject matter (e.g., a system) may comprise: a signal receiver circuit configured to receive first and second physiologic information of a patient, the second physiologic information different than the first physiologic information, the first physiologic information cyclic with patient respiration; and an assessment circuit configured to determine first respiration phase information of the first physiologic information, the first respiration phase information indicative of inspiration and expiration of the patient and to determine a composite respiration phase of the patient using the determined first respiration phase information and the second physiologic information.

In Example 2, the subject matter of Example 1 may optionally be configured such that the assessment circuit is configured to: determine a first phase correction factor for the determined first respiration phase information using the second physiologic information; and determine the composite respiration phase of the patient using the determined first respiration phase information and the determined first phase correction factor.

In Example 3, the subject matter of any one or more of Examples 1-2 may optionally be configured such that, to determine the composite respiration phase of the patient, the assessment circuit is configured to adjust the determined first respiration phase information by the first phase correction factor.

In Example 4, the subject matter of any one or more of Examples 1-3 may optionally be configured such that the second physiologic information is cyclic with patient respiration.

In Example 5, the subject matter of any one or more of Examples 1-4 may optionally be configured such that the assessment circuit is configured to: determine second respiration phase information of the second physiologic information, the second respiration phase information indicative of inspiration and expiration of the patient; and determine the composite respiration phase of the patient using the determined first and second respiratory phase information.

In Example 6, the subject matter of any one or more of Examples 1-5 may optionally be configured such that the assessment circuit is configured to: determine a first phase correction factor for the determined first respiration phase information using the determined second respiratory phase information; and determine the composite respiration phase of the patient using the determined first respiration phase information and the determined first phase correction factor.

In Example 7, the subject matter of any one or more of Examples 1-6 may optionally be configured such that, to determine the composite respiration phase of the patient, the assessment circuit is configured to adjust the determined first respiration phase information by the first phase correction factor.

In Example 8, the subject matter of any one or more of Examples 1-7 may optionally be configured such that the assessment circuit comprises: a first phase lock loop (PLL) circuit configured to receive the first physiologic information and provide a first PLL output; a second PLL circuit configured to receive the second physiologic information and provide a second PLL output, wherein the assessment circuit is configured to align the first PLL output to the second PLL output using the determined first phase correction factor, and to combine the aligned first PLL output and the second PLL output, and wherein the assessment circuit is configured to determine the composite respiration phase of the patient using the combined aligned first PLL output and the second PLL output.

In Example 9, the subject matter of any one or more of Examples 1-8 may optionally be configured such that the assessment circuit is to determine a change in patient status, to detect a physiological condition of the patient, or to determine a patient therapy parameter using a determined change in the first respiration phase information over time relative to the second respiration phase information over time or the determined composite respiration phase of the patient over time.

In Example 10, the subject matter of any one or more of Examples 1-9 may optionally be configured such that the first and second physiologic information comprise different types of information comprising two or more of electrocardiogram information of the patient, accelerometer information of the patient, or blood flow information of the patient.

In Example 11, the subject matter of any one or more of Examples 1-10 may optionally be configured such that the first physiologic information comprises information from a first physiologic signal over a first period, the second physiologic information comprises information from a second physiologic signal different than the first physiologic signal over a second period, wherein the first and second periods at least partially overlap, wherein electrocardiogram information of the patient comprises R-wave amplitude information of the patient or electrocardiogram heart rate information of the patient, and wherein accelerometer information of the patient comprises accelerometer information indicative of patient chest motion.

In Example 12, the subject matter of any one or more of Examples 1-11 may optionally be configured such that the assessment circuit is configured to determine a respiratory parameter using the composite respiration phase, and wherein the respiratory parameter comprises at least one of an inspiration to expiration (I/E) ratio or respiratory sounds.

An example (e.g., "Example 13") of subject matter (e.g., a method) may comprise: receiving, at a signal receiver circuit, first and second physiologic information of a patient, the second physiologic information different than the first physiologic information, the first physiologic information cyclic with patient respiration: determining, using an assessment circuit, first respiration phase information of the first physiologic information, the first respiration phase information indicative of inspiration and expiration of the patient; and determining, using the assessment circuit, a composite respiration phase of the patient using the determined first respiration phase information and the second physiologic information.

In Example 14, the subject matter of Example 13 may optionally comprise determining, using the assessment circuit, a first phase correction factor for the determined first respiration phase information using the second physiologic information, wherein determining the composite respiration phase of the patient comprises using the determined first respiration phase information and the determined first phase correction factor.

In Example 15, the subject matter of any one or more of Examples 1-14 may optionally comprise: determining, using the assessment circuit, second respiration phase information of the second physiologic information, the second physiologic information cyclic with patient respiration, the second respiration phase information indicative of inspiration and expiration of the patient; and determining, using the assessment circuit, a first phase correction factor for the determined first respiration phase information using the determined second respiratory phase information, wherein determining the composite respiration phase of the patient comprises using the determined first respiration phase information and the determined first phase correction factor.

In Example 16, the subject matter of any one or more of Examples 1-15 may optionally be configured such that, to determine the composite respiration phase of the patient, the assessment circuit is configured to adjust the determined first respiration phase information by the first phase correction factor.

In Example 17, the subject matter of any one or more of Examples 1-16 may optionally be configured such that determining first respiration phase information of the first physiologic information comprises: receiving the first physiologic information using a first phase lock loop (PLL) circuit and providing a first PLL output; and receiving the second physiologic information using a second PLL circuit and providing a second PLL output, and wherein determining the composite respiration phase of the patient comprises: aligning the first PLL output to the second PLL output using the determined first phase correction factor; and combining the aligned first PLL output and the second PLL output.

In Example 18, the subject matter of any one or more of Examples 1-17 may optionally be configured such that the first and second physiologic information comprise different types of information comprising two or more of electrocardiogram information of the patient, accelerometer information of the patient, or blood flow information of the patient, wherein the first physiologic information comprises information from a first physiologic signal over a first period, the second physiologic information comprises information from a second physiologic signal different than the first physiologic signal over a second period, wherein the first and second periods at least partially overlap, wherein electrocardiogram information of the patient comprises R-wave amplitude information of the patient or electrocardiogram heart rate information of the patient, and wherein accelerometer information of the patient comprises accelerometer information indicative of patient chest motion, wherein the method comprises: determining, using the assessment circuit, a respiratory parameter using the composite respiration phase, and wherein the respiratory parameter comprises at least one of an inspiration to expiration (I/E) ratio or respiratory sounds.

An example (e.g., "Example 19") of subject matter (e.g., at least one machine-readable medium) may comprise instructions that, when performed by a medical device, cause the medical device to: receive first and second physiologic information of a patient, the second physiologic information different than the first physiologic information, the first physiologic information cyclic with patient respiration; determine first respiration phase information of the first physiologic information, the first respiration phase information indicative of inspiration and expiration of the patient; and determine a composite respiration phase of the patient using the determined first respiration phase information and the second physiologic information.

In Example 20, the subject matter of Example 19 may optionally be configured such that the instructions, when performed by the medical device, cause the medical device to: determine second respiration phase information of the second physiologic information, the second physiologic information cyclic with patient respiration, the second respiration phase information indicative of inspiration and expiration of the patient; and determine a first phase correction factor for the determined first respiration phase information using the determined second respiratory phase information, wherein to determine the composite respiration phase of the patient comprises using the determined first respiration phase information and the determined first phase correction factor.

In Example 21, subject matter (e.g., a system or apparatus) may optionally combine any portion or combination of any portion of any one or more of Examples 1-20 to comprise "means for" performing any portion of any one or more of the functions or methods of Examples 1-20, or at least one "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
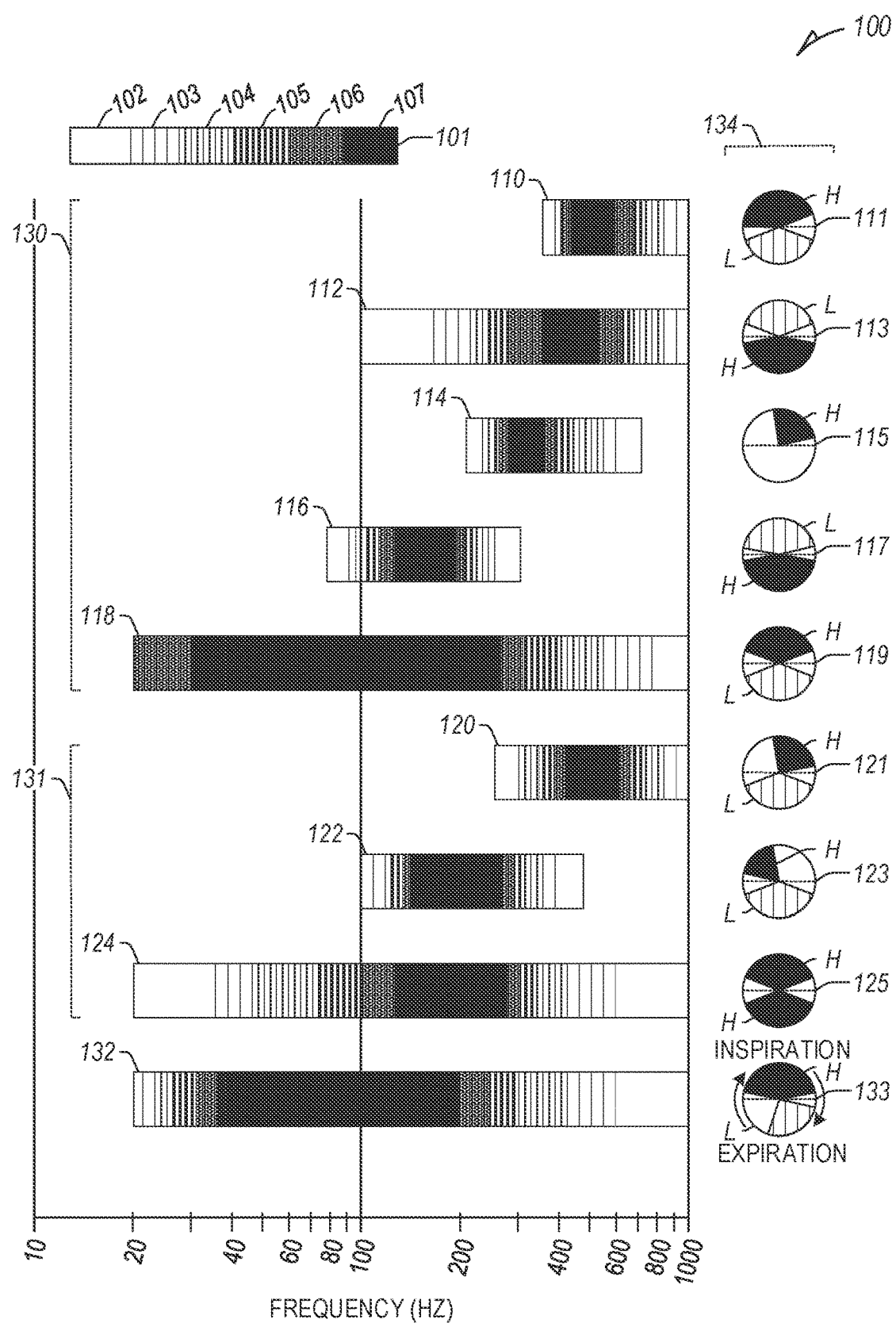
FIG. 1 illustrates example intensities of respiratory sounds.

Direct airflow measurements (e.g., direct oronasal airflow measurements) can be obtained using a variety of external sensors or transducers (e.g., external pressure sensors, thermistors, piezoelectric sensors, airflow sensors, etc.) placed on or about the airway of a patient, including in, on, or near a nose or a mouth of the patient, and can include a spirometer, a pressure sensor, a thermistor, a piezoelectric sensor, etc., each in fluid communication (direct contact) with patient airflow into or out of the body. Other traditional external respiration detection can include a belt to detect expansion or contraction of the chest or abdomen associated with respiration. However, expansion and contraction of the chest or abdomen of a patient generally leads direct airflow measurement.

Conceptually, the respiration phase begins with airway muscle movement (e.g., movement of the diaphragm, etc.) and movement of the chest and abdomen, leading to thoracic pressure changes, patient airflow, and respiration sounds. Thoracic pressure changes impact other physiologic information, such as heart rate, arterial pressure, and tissue perfusion.

The present inventor has recognized, among other things, systems and methods to determine a composite respiration phase measurement of a patient using one or more physiologic signals having respiratory information (e.g., indirect respiration measurements) separate from traditional direct oronasal airflow measurement, such as one or more of an electrocardiogram (ECG) signal, an accelerometer signal, a photoplethysmography (PPG) signal, or one or more other physiologic signals having respiration information for indirect respiration measurement, different than direct airflow measurement. However, the peaks and valleys of such indirect respiration measurements may lead or lag the peaks and valleys of traditional direct oronasal airflow measurement, and accordingly, determination of patient respiratory phase information, including inspiration, expiration, or transitions therebetween using such indirect respiration measurements may differ from patient inspiration or expiration determined using direct oronasal airflow.

The present inventor has further recognized systems and methods to automatically align different indirect respiration measurements to patient airflow. In certain examples, multiple indirect respiration measurements can be aligned using one or more phase correction factors improve patient respiration phase determination. Each physiologic signal can have a specific phase correction. The phase correction of respective signals can vary between patients, in certain examples, according to one or more other physiologic signals.

An improvement in the accuracy of respiratory phase information can improve the sensitivity of one or more other respiratory parameters. For example, determination of respiratory phase is required to determine an inspiration/expiration (I/E) ratio, a forced expiratory volume (FEV) over time (e.g., FEV over 1 second (FEV1)), or a forced vital capacity (FVC), etc. Other respiratory parameters that can benefit from accurate respiratory phase information, including respiratory rate (RR), tidal volume (TV), respiratory sounds, etc. In other examples, certain cardiac parameters can benefit from accurate respiratory phase information, such as murmurs, etc.

FIG. 1 illustrates example intensities of respiratory sounds 100 in frequency (Hz) and phase according to a scale 101 varying in intensity level from a first intensity level 102 (less intensity) to a sixth intensity level 107 (more intensity). The respiratory sounds 100 include continuous sounds 130, discontinuous sounds 131, and normal vesicular breathing 132 ranging in frequency between 20 and 1000 Hz and varying in intensity across different frequencies. In an example, a determined composite respiration phase of the patient can be used to discriminate different respiratory sounds, such as those illustrated herein, etc.

For example, the continuous sounds 130 include stridor 110 centered about 500 Hz, wheeze 112 centered about 400 Hz, squawk 114 centered about 300 Hz, rhonchus 116 centered about 150 Hz, and snoring 118 centered about 100 Hz. The discontinuous sounds 131 include fine crackles 120 centered about 500 Hz, coarse crackles 122 centered about 200 Hz, and pleural friction rub 124 centered about 200 Hz. Normal vesicular breathing 132 is centered about 100 Hz.

The frequency of a specific respiratory sound aids identification of the specific sound. However, as nearly all of these sounds have at least some overlap, and in many cases, substantial overlap in frequency range and response, other information is used to aid identification, including, for example, the portion of the respiratory phase in which such specific sound occurs.

Respiratory phase information 134 for each of the respiratory sounds 100 are illustrated using a circle, the top half (identified using a dashed line) indicating inspiration and the bottom half indicating expiration with transitions between inspiration and expiration at the dashed lines. For example, normal vesicular breathing respiratory phase information 133 indicates more energy during inspiration, for a substantial portion of the inspiration cycle, and less energy during the early phase of expiration. In contrast, snoring respiratory phase information 119 indicates more energy during inspiration (similar to normal vesicular breathing 132), and less energy during expiration, but over a larger portion of the expiration than normal vesicular breathing respiratory phase information 133. Thus, snoring 118 and normal vesicular breathing 132, both centered about 100 Hz, can be distinguished using detected differences in respiratory phase information 134. However, more accurate detection of respiratory phase, or respiratory phase changes (between inspiration and expiration), provide more accurate determination of respiratory sounds 100.

Stridor respiratory phase information 111 indicates more energy earlier in inspiration, and less energy through a longer portion of expiration, than normal vesicular breathing 132. Wheeze respiratory phase information 113 indicates more energy through a large portion of expiration and less energy through a large portion of inspiration. Squawk respiratory phase information 115 indicates more energy during the latter portion of inspiration and little to no energy during expiration. Rhonchus respiratory phase information 117 indicates more energy through a large portion of expiration and less energy through a large portion of inspiration. Snoring respiratory phase information 119 indicates more energy during a large portion of inspiration and less energy during a large portion of expiration. Fine crackle respiratory phase information 121 indicates more energy during the latter portion of inspiration and less energy through a large portion of expiration. Coarse crackle respiratory phase information 123 indicates more energy during the earlier portion of inspiration and less energy through a large portion of expiration. Pleural friction rub respiratory phase information 125 indicates more energy during a large portion of inspiration as well through a large portion of expiration.

Figure 2:
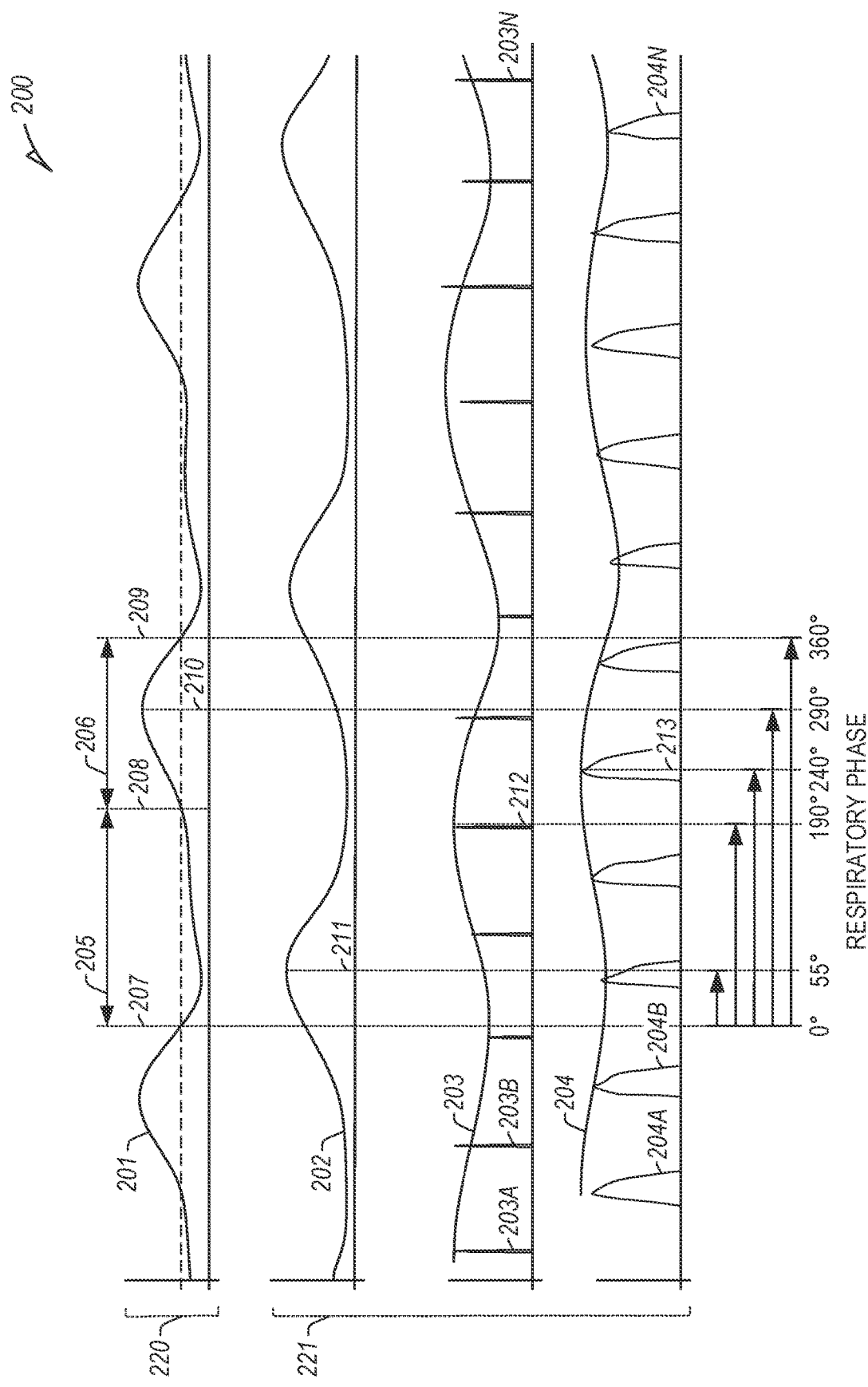
FIGS. 2 and 3 illustrate example respiratory signals.

FIG. 2 illustrates example respiratory phase differences 200 between different respiration signals including a direct respiration measurement 220 and several indirect respiration measurements 221. The direct respiration measurement 220 includes an oronasal airflow signal 201 (e.g., an oral-nasal pressure signal). The indirect respiration measurements 221 include an impedance respiration signal 202 (e.g., an impedance pneumography), an ECG respiration signal 203 (determined using R-wave peaks 203A-N of an ECG signal), and a PPG respiration signal 204 (determined using PPG peaks 204A-N of a PPG signal).

Periods of inspiration 205 and expiration 206 are marked at zero-crossings of the oronasal airflow signal 201, including a first zero-crossing 207 marking a transition from positive airflow to negative airflow (the beginning of inspiration 205), a second zero-crossing 208 marking a transition from negative airflow to positive airflow (the end of inspiration 205 and beginning of expiration 206), and a third zero-crossing 209 marking a transition from positive airflow to negative airflow (the end of expiration 206 and beginning of a subsequent respiratory phase).

The challenges in accurately determining respiratory phase are multifaceted. One way to determine respiratory phase information from indirect respiration measurements 221, such as physiologic signals having a respiratory component, is by detecting peaks in components of the physiologic signal having respiratory information. For example, the ECG respiration signal 203 illustrated in FIG. 2 is determined using an average R-wave amplitude of multiple R-wave peaks 203A-N of ECG information of a patient, and the PPG respiration signal 204 is determined using an average PPG signal amplitude of multiple PPG peaks 204A-N of PPG information of the patient.

Certain respiratory parameters, such as respiration frequency, can be determined using the number and location of detected peaks. However, the peaks often do not uniformly correspond to a specific portion of a respiratory phase. For example, with respect to the first zero-crossing 207 corresponding to inspiration 205 being 0° of a respiratory phase (having 360° between successive inspiration periods), an impedance peak 211 is at 55°, an ECG peak 212 is at 190°, a PPG peak 213 is at 240° an oronasal peak 210 is at 290°. The third zero-crossing 209 closes the respiratory phase at 360°. As there are no indirect respiration measurement peaks about 0°/360°, such transition (the first or third zero-crossing 207, 209) is often estimated following one or more other detected peaks. The second zero-crossing 208 occurs at approximately 200° (different than the illustrated 180° respiratory phase information 134 in FIG. 1). Although the second zero-crossing relatively closely follows the ECG peak 212, estimation is again often required.

The challenge is amplified in that inspiration and expiration can have different period lengths, with inspiration 205 often longer than expiration 206. Further, in certain examples, one or both of peaks and troughs can be difficult to identify. For example, the impedance respiration signal 202 has a defined peak (e.g., at impedance peak 211), but the trough is more difficult to identify. In certain examples, the signal can be inverted, such as depending on sensor (e.g., one or more electrodes) polarity, placement, or one or more other factors. Accurate detection of periods of inspiration 205 and expiration 206 are important, such as to detect the I/E ratio, etc. Further, in certain examples, respiratory phase information can be scaled for display to reflect desired information. For example, the period lengths of inspiration 205 and expiration 206 in FIG. 2, approximately 200° and 160°, respectively, can be scaled to reflect equal phase distributions of 1800, such as illustrated in the respiratory phase information 134 of FIG. 1.

Figure 3:
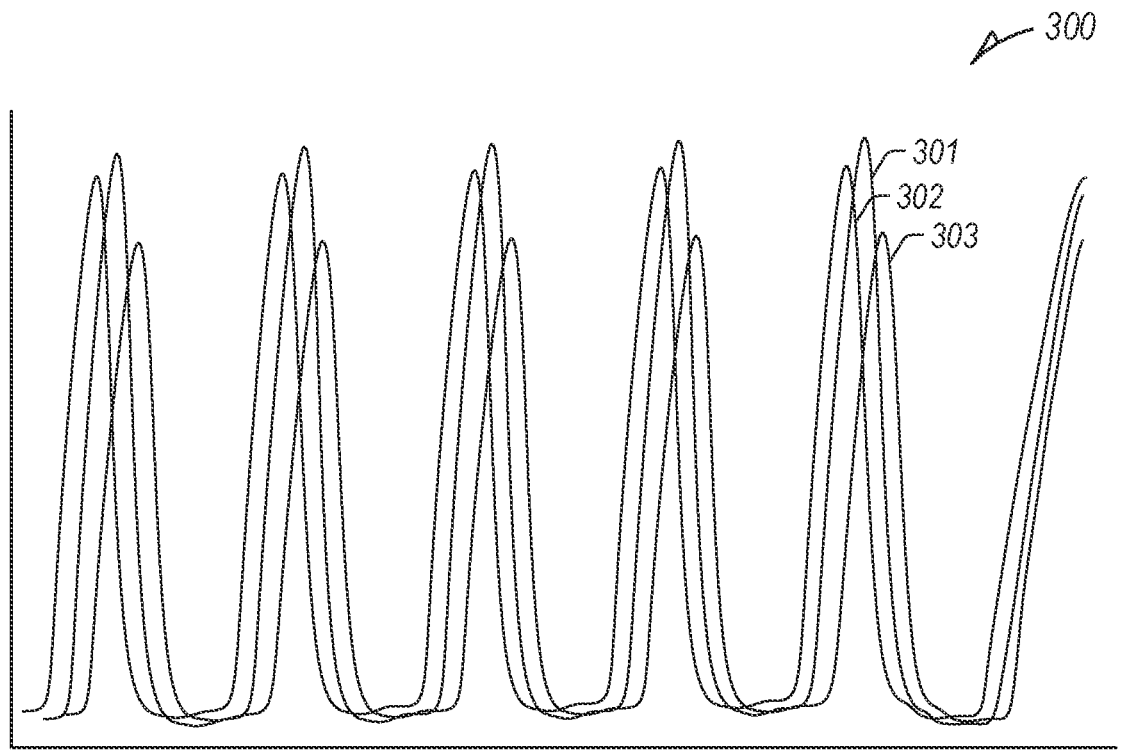

FIG. 3 illustrates example respiration signals 300 having different phase shifts, including first, second, and third respiration signals 301, 302, 303. In an example, the first respiration signal 301 can include an impedance respiration signal, the second respiration signal 302 can include an ECG respiration signal, and the third respiration signal 303 can include a PPG respiration signal. In other examples, the respiration signals 300 can include one or more other physiologic signals having other physiologic signals having a respiratory component.

To determine accurate respiration phase information, the present inventor has recognized, among other things, that phase correction factors can be used to align respiration measurements to the actual respiration phase of the patient (e.g., the phase of a direct measurement of patient airflow). Such phase correction factors can be population-based, patient-specific, or combinations thereof. Further, individual physiologic signal measurement may include large amounts of noise. To increase signal integrity, a composite of multiple physiologic signals having respiratory components can be combined, for example, after alignment using one or more correction factors. In an example, one or more phase lock loop (PLL) circuits, such as of a medical device or one or more other components associated with a medical-device system, can be used to align the multiple physiologic signals.

Figure 4:
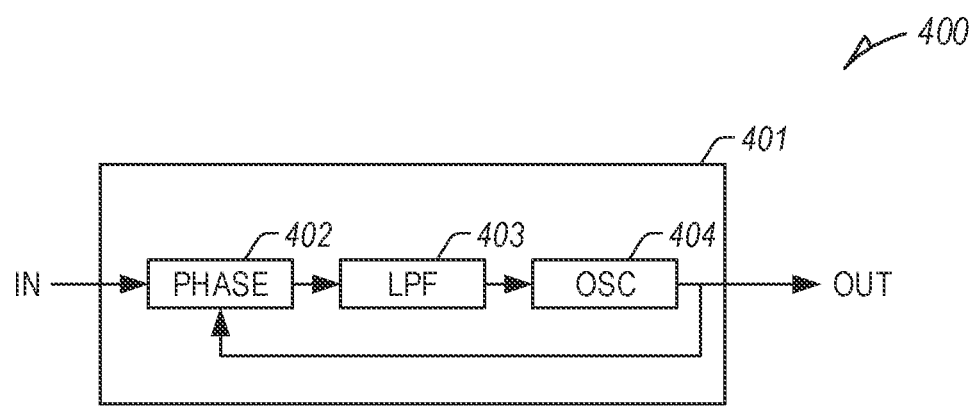
FIG. 4 illustrates an example phase correction circuit.

FIG. 4 illustrates an example phase correction circuit 400 including a phase lock loop (PLL) circuit 401 configured to receive an input signal (IN) (e.g., physiologic information, such as from a physiologic signal having imperfect respiratory information, etc.) and provide an output signal (OUT). In an example, the input signal can often be noisy, unstable, or non-sinusoidal. The PLL circuit 401 can be configured to provide an output signal, based on the input signal, having a clear, stable frequency and sinusoidal phase.

The PLL circuit 401 include a phase comparator (PHASE) circuit 402, a low-pass filter (LPF) circuit 403, and an oscillator (OSC) circuit 404. The phase comparator circuit 402 can ensure that the output signal maintains a relatively consistent phase angle in relation to the input signal, such as by determining a phase difference between the input signal and the output signal and providing an output signal representative of the difference. The low-pass filter 403 can filter high frequency noise from the output of the phase comparator circuit 402. The oscillator circuit 404 (e.g., an amplitude-controlled oscillator, etc.) can receive the filtered output of the low-pass filter 403 and provide an output signal (e.g., a sinusoidal output signal) having a frequency controlled by the output of the low-pass filter 403.

In certain examples, the phase correction circuit 400 or the PLL circuit 401 can include one or more other components or circuits. In an example, the PLL circuit 401 can include a loop filter circuit or one or more other circuits or components configured to control the feedback from the output of the oscillator circuit 404 to the phase comparator circuit 402, such as to control the stability of the loop, the speed or responsiveness of the loop, etc. Although described and illustrated herein as a sinusoidal output signal, in other examples, the output signal (OUT) can take one or more other shapes or forms, such as a square-wave output, a sawtooth-wave output, etc.

Figure 6:
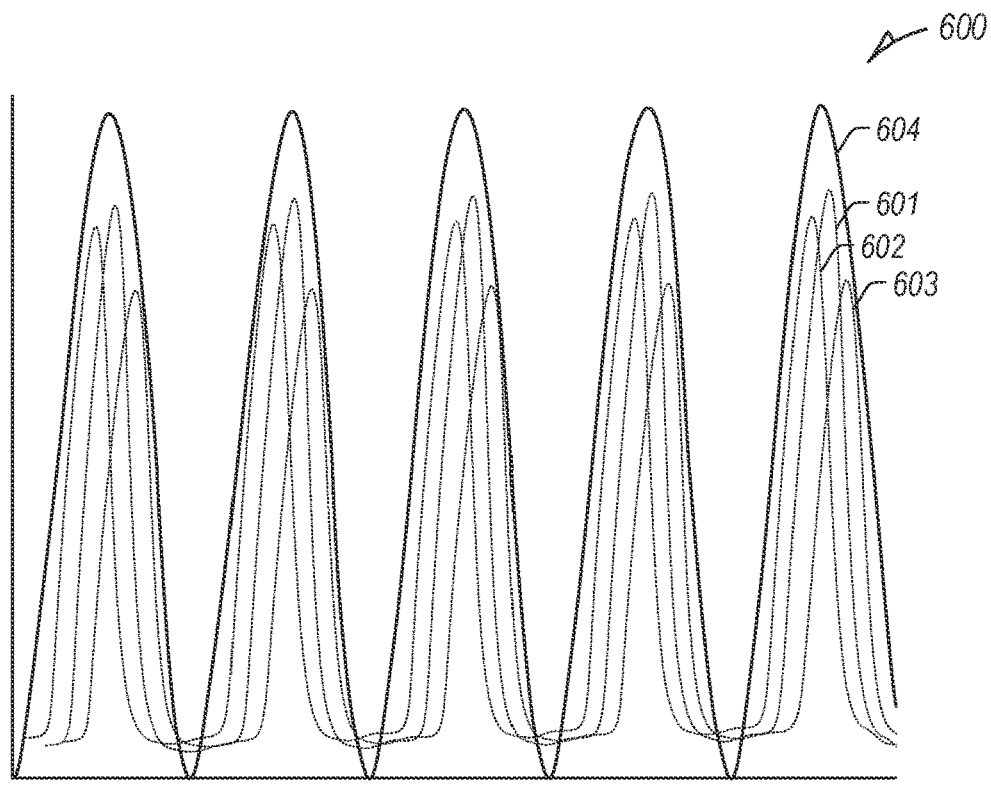
FIG. 6 illustrates an example respiration signals and an output signal.

In certain examples, the PLL circuit 401 can receive a respiration signal (e.g., a non-sinusoidal respiration signal), such as one or more of the respiration signals 300 of FIG. 3, and provide a sinusoidal output, such as an output signal 604 illustrated in FIG. 6, for each received respiration signal, or for a composite of multiple respiration signals or received patient respiration information.

Figure 5:
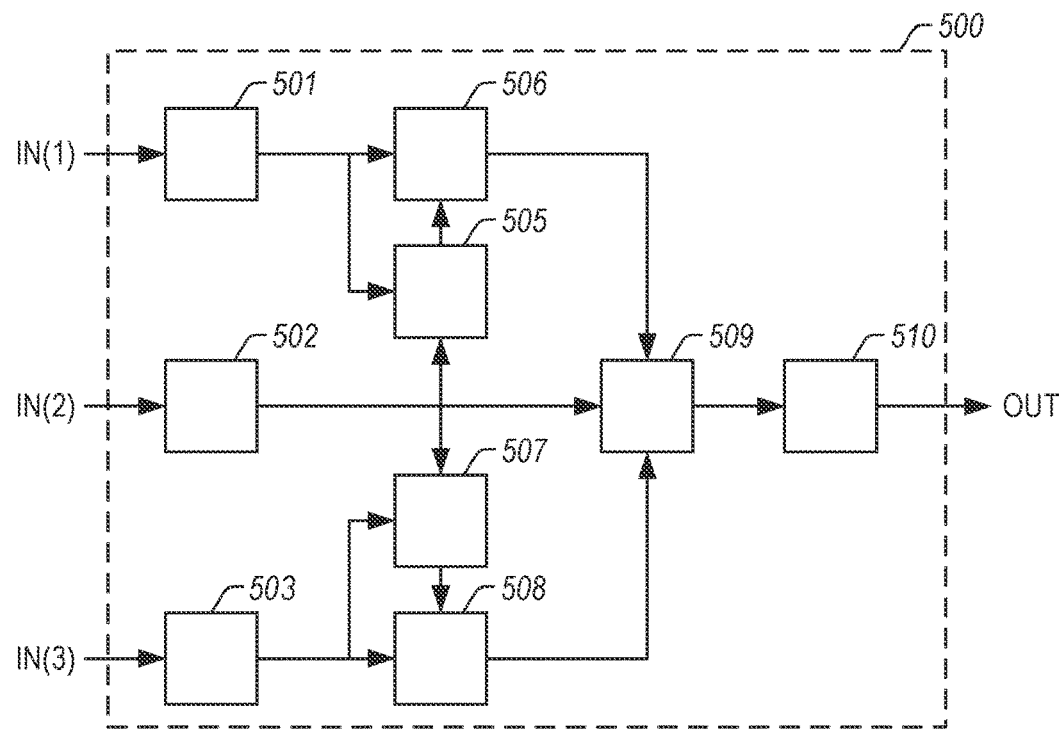
FIG. 5 illustrates an example assessment circuit.

FIG. 5 illustrates an example assessment circuit 500, or portion of an assessment circuit 500 configured to receive one or more input signals and provide an output signal (OUT). The assessment circuit 500 can include first, second, and third PLL circuits 501, 502, 503 (e.g., the same as or similar to the PLL circuit 401 illustrated in FIG. 1). Each of the first, second, and third PLL circuits 501, 502, 503 can be configured to receive one or more respective input signals (e.g., IN(1), IN(2), and IN(3), etc.) and generate one or more respective output signals (e.g., OUT(1), OUT(2), and OUT (3), etc.). The one or more input signals can include physiologic signals having respiratory information, such as an ECG signal, an accelerometer signal, an impedance signal, a PPG signal, etc. In an example, the assessment circuit 500 can be configured to receive, as respective input signals, the respiration signals 300 illustrated in FIG. 3.

The assessment circuit 500 can include circuits or components configured to align outputs of one or more of the PLL circuits to another output of the PLL circuits or to one or more other signals (e.g., one or more other physiologic signals, etc.). In an example, the assessment circuit 500 can include one or more phase detector circuits and one or more phase compensator circuits configured to detect a phase of one or more outputs of the PLL circuits and to align the one or more outputs, such as to align the outputs of the first and third PLL circuits 501, 503 to the output of the second PLL circuit 502, as illustrated in FIG. 5.

In the example of FIG. 5, a first phase detector 505 can detect a phase difference between the outputs of the first and second PLL circuits 501, 502 and provide a signal representative of the difference to a first phase compensator circuit 506. The first phase compensator circuit 506 can align the output of the first PLL circuit 501 to the output of the second PLL circuit 502. A second phase detector circuit 507 can detect a phase difference between the outputs of the second and third PLL circuits 502, 503 and provide a signal representative of the difference to a second phase compensator circuit 508. The second phase compensator circuit 508 can align the output of the third PLL circuit 503 to the output of the second PLL circuit 502. In other examples, the outputs of the first and second PLL circuits 501, 502 can be aligned to the output of the third PLL circuit 503, or the outputs of the second and third PLL circuits 502, 503 can be aligned to the output of the first PLL circuit 501. In other examples, the assessment circuit 500 can include more or less PLL circuits configured to align one or more outputs with an output of another PLL circuit, or to align one or more other outputs with one or more other physiologic signals or physiologic information from the patient.

The assessment circuit 500 can include an adder circuit 509 configured to combine (e.g., add, average, etc.) the aligned signals, such as to combine the outputs of the first phase compensator circuit 506, the second phase compensator circuit 508, and in the example of FIG. 5, the second PLL circuit 502, and to provide a composite output signal. The assessment circuit 500 can include a fourth PLL circuit 510 configured to receive the composite output from the adder circuit 509 and provide an output signal (OUT) comprising separate signal and phase outputs, including information illustrated in FIGS. 6 and 7, respectively.

In other examples, the assessment circuit 500 can include one or more additional circuits or components.

FIG. 6 illustrates an example respiration signals 600 including first, second, and third respiration signals 601, 602, 603 (e.g., similar to or the same as the first, second, and third respiration signals 301, 302, 303), and an output signal 604, such as determined using the first, second, and third respiration signals 601, 602, 603. In an example, the output signal 604 can include an output (OUT) of the example assessment circuit 500 of FIG. 5.

Figure 7:
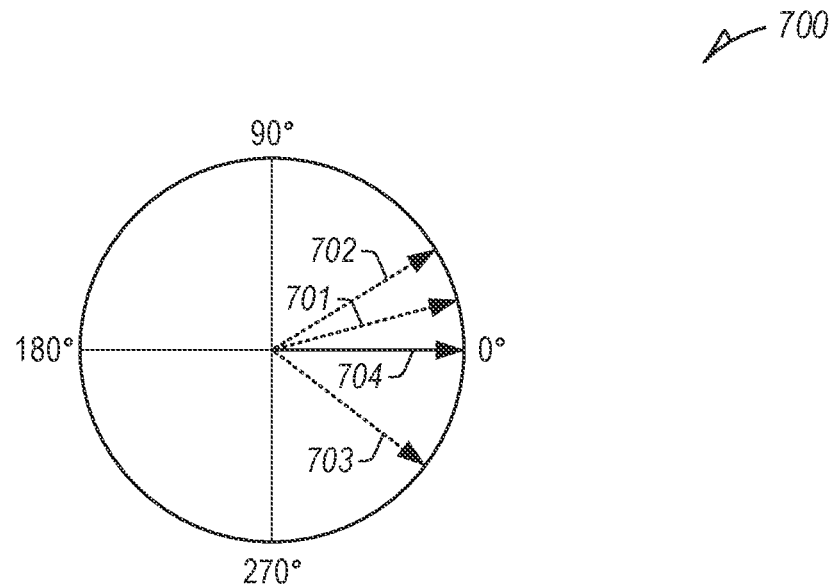
FIG. 7 illustrates an example phase output of multiple respiration signals.

FIG. 7 illustrates an example phase output 700 of multiple respiration signals, such as the respiration signals 600 illustrated in FIG. 6. The phase output 700 can include first, second, third, and fourth phase outputs 701-704. In an example, the fourth phase output 704 can be indicative of a phase of an output signal, or a combination or composite of multiple respiration signals, such as the first, second, and third respiration signals 601, 602, 603 of FIG. 6.

The first phase output 701 can be indicative of a phase of a first respiration signal, such as of the first respiration signal 601 of FIG. 6, with respect to the fourth phase output 704 (0°). The second phase output 702 can be indicative of a phase of a second respiration signal, such as the second respiration signal 602 of FIG. 6, with respect to the fourth phase output 704. The third phase output 703 can be indicative of a phase of a third respiration signal, such as the third respiration signal 603 of FIG. 6, with respect to the fourth phase output 704.

In certain examples, the direction and delay of each of the respiration signals can be patient specific. In one example, although variable, phase shifts for certain parameters, with respect to direct measurement of patient airflow (0°), can be expected as illustrated in Table 1 (with positive numbers indicating phase lag).

TABLE 1

Example Respiration Phase Shift

| Physiologic Signal | Chest Movement | ECG R Wave Amplitude | ECG Heart Rate | PPG | Arterial Pressure |
|---|---|---|---|---|---|
| Phase Shift Relative to Airflow | −70° | 0° | +55° | +85° | +50° |

In an example, for implantable medical devices, a common signal fiducial (e.g., a peak value, a zero-cross value, etc.) can be identified or measured at implant or programming to determine phase shift among different signals. In certain examples, signal fiducials can be identified or measured at implant or programming at different controlled configurations or situations (e.g., different postures, different activity levels, etc.) or during different doses of a therapy (e.g. medication, continuous positive airway pressure (CPAP) or other respiratory therapy, cardiac pacing, neuro-modulation) wherein the different dose might include no dose of a therapy. Initial values or measurements can be used to control combination of different physiologic signals, or as an initial data point for later combination or adjustment.

In certain examples, the direction and delay of respiration phase shifts can be used to track or determine patient health status or changes in patient health, such as disease state changes, etc. For example, modulation of physiologic information due to respiration can decrease due to fluid overflow or shallow breathing. Accordingly, decreased phase shifts of patient physiologic information relative to patient airflow can be indicative of heart failure, or a worsening or change in heart failure status. Modulation of physiologic information due to respiration can increase due to airway obstruction or increased thoracic pressure. Accordingly, increased phase shifts of patient physiologic information relative to patient airflow can be indicative of chronic obstructive pulmonary disease (COPD) or asthma, or a worsening or change in COPD or asthma status.

In an example, the direction and delay of respiration phase shifts can be used to track or determine therapy effectiveness, such as a medication therapy, continuous positive airway pressure or other respiratory therapy, cardiac pacing therapy, or neuro-modulation therapy. For example, nebulizer therapy can be used to reduce airway congestion associated with COPD or asthma. Reduced phase shifts of patient physiologic information relative to patient airflow can be indicative of improvement in airway congestion due to effective nebulizer therapy.

Modulation of physiologic information due to respiration can cease during an apnea event. Accordingly, severe and unstable phase shifts for several (e.g., 5-10) respiration cycles after resolution of the apnea can be indicative of an apnea event. Modulation of physiologic information due to respiration can decrease during a hypopnea event. Accordingly, moderate but unstable phase shifts for several (e.g., 5-10) respiration cycles can be indicative of a hypopnea event, or resolution of a hypopnea event.

Modulation of physiologic information due to respiration can decrease due to shallow breathing, such as indicative of patient pneumonia. Accordingly, decreased phase shifts of patient physiologic information relative to patient airflow can be indicative of shallow breathing, patient pneumonia, or a worsening or change in shallow breathing or patient pneumonia.

Figure 8:
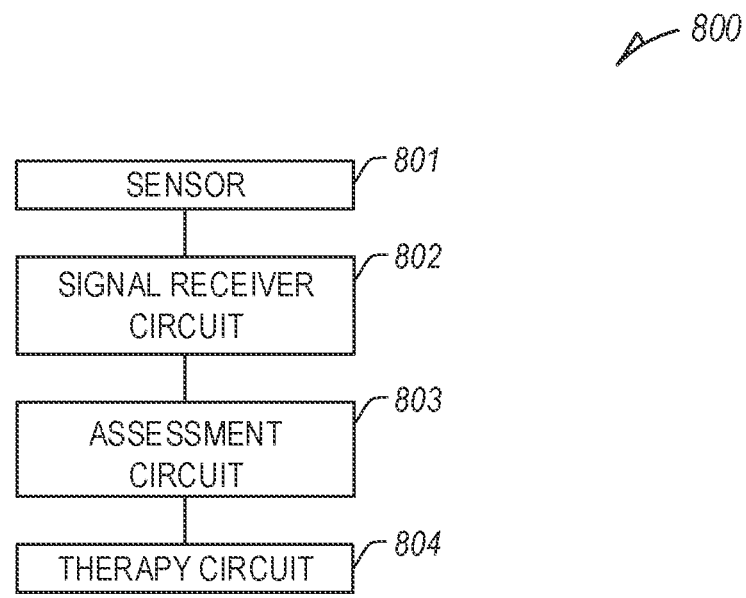
FIG. 8 illustrates an example system.

FIG. 8 illustrates an example system 800, such as a medical-device system, etc. In an example, one or more aspects of the example system 800 can be a component of, or communicatively coupled to, an ambulatory medical device (AMD). AMDs can be configured to monitor, detect, or treat various physiologic conditions of the body, such as cardiac conditions associated with a reduced ability of a heart to sufficiently deliver blood to a body, including HF, arrhythmias, hypertension, dyssynchrony, etc. AMDs can include a single device or a plurality of medical devices or monitors implanted in a patient's body or otherwise positioned on or about the patient to monitor patient physiologic information of the patient, such as using one or more sensors, the physiologic information including one or more of heart sounds, respiration (e.g., respiration rate, tidal volume (TV), etc.), impedance (e.g., thoracic impedance, cardiac impedance, cutaneous impedance, etc.), pressure (e.g., blood pressure), cardiac activity (e.g., heart rate, cardiac electrical information, etc.), chemical (e.g., electrolyte), physical activity, posture, plethysmography, or one or more other physiologic parameters of a patient, or to provide electrical stimulation or one or more other therapies or treatments to the patient.

The example system 800 can include a signal receiver circuit 802 and an assessment circuit 803. The signal receiver circuit 802 can be configured to receive physiologic information of a patient (or group of patients) from one or more sensors 801. The assessment circuit 803 can be configured to receive information from the signal receiver circuit 802, and to determine one or more parameters (e.g., physiologic parameters, stratifiers, etc.) or existing or changed patient conditions (e.g., indications of patient dehydration, a respiratory condition (e.g. COPD, asthma), a cardiac condition (e.g. heart failure, arrhythmia), etc.) using the received physiologic information, such as described herein. The physiologic information can include, among other things, cardiac electrical information, impedance information, respiration information, heart sound information, activity information, posture information, temperature information, chemical information, etc.

In an example, the sensor 801 can include one or more of: a respiration sensor configured to receive respiration information (e.g., a respiration rate, a respiration volume (tidal volume), etc.); an acceleration sensor (e.g., an accelerometer, a microphone, etc.) configured to receive cardiac acceleration information (e.g., cardiac vibration information, pressure waveform information, heart sound information, endocardial acceleration information, acceleration information, activity information, posture information, etc.); an impedance sensor (e.g., intrathoracic impedance sensor, transthoracic impedance sensor, etc.) configured to receive impedance information, a cardiac sensor configured to receive cardiac electrical information; an activity sensor configured to receive information about a physical motion (e.g., activity, steps, etc.); a posture sensor configured to receive posture or position information; a pressure sensor configured to receive pressure information; a plethysmograph sensor (e.g., a photoplethysmography sensor, etc.); a chemical sensor (e.g., an electrolyte sensor, a pH sensor, an anion gap sensor, etc.); a skin temperature sensor; a skin elasticity sensor, or one or more other sensors configured to receive physiologic information of the patient.

The assessment circuit 803 can be configured to provide an output to a user, such as to a display or one or more other user interface, the output including a score, a trend, an alert, or other indication. In other examples, the assessment circuit 803 can be configured to provide an output to another circuit, machine, or process, such as a therapy circuit 804 (e.g., a cardiac resynchronization therapy (CRT) circuit, a chemical therapy circuit, etc.), etc., to control, adjust, or cease a therapy of a medical device, a drug delivery system, etc., or otherwise alter one or more processes or functions of one or more other aspects of a medical-device system, such as one or more CRT parameters, drug delivery, dosage determinations or recommendations, etc. In an example, the therapy circuit 804 can include one or more of a stimulation control circuit, a cardiac stimulation circuit, a neural stimulation circuit, a dosage determination or control circuit, etc. In other examples, the therapy circuit 804 can be controlled by the assessment circuit 803, or one or more other circuits, etc.

AMDs can include a range of medical devices, including, for example, traditional cardiac rhythm management (CRM) devices, such as pacemakers, defibrillators, or cardiac resynchronizers, include implantable or subcutaneous devices configured to be implanted in a chest of a patient. The CRM device can include one or more leads to position one or more electrodes or other sensors at various locations in or near the heart, such as in one or more of the atria or ventricles. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from the patient, or provide one or more therapies or stimulation to the patient.

Implantable devices can additionally or separately include leadless cardiac pacemakers (LCP), small (e.g., smaller than traditional implantable CRM devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

Each additional sensor within or associated with an AMD or medical device system can increase system cost and complexity, reduce system reliability, or increase the power consumption and reduce the usable life of the AMD. Accordingly, it can be beneficial to use a single sensor to determine multiple types of physiologic information, or a smaller number of sensors to measure a larger number of different types of physiologic information. For example, it can be beneficial to detect atrial cardiac electrical information without a lead or an electrode in, or in contact with, the atria. Similarly, it can be beneficial to detect accurate respiration phase information without a direct measurement of patient airflow.

Figure 9:
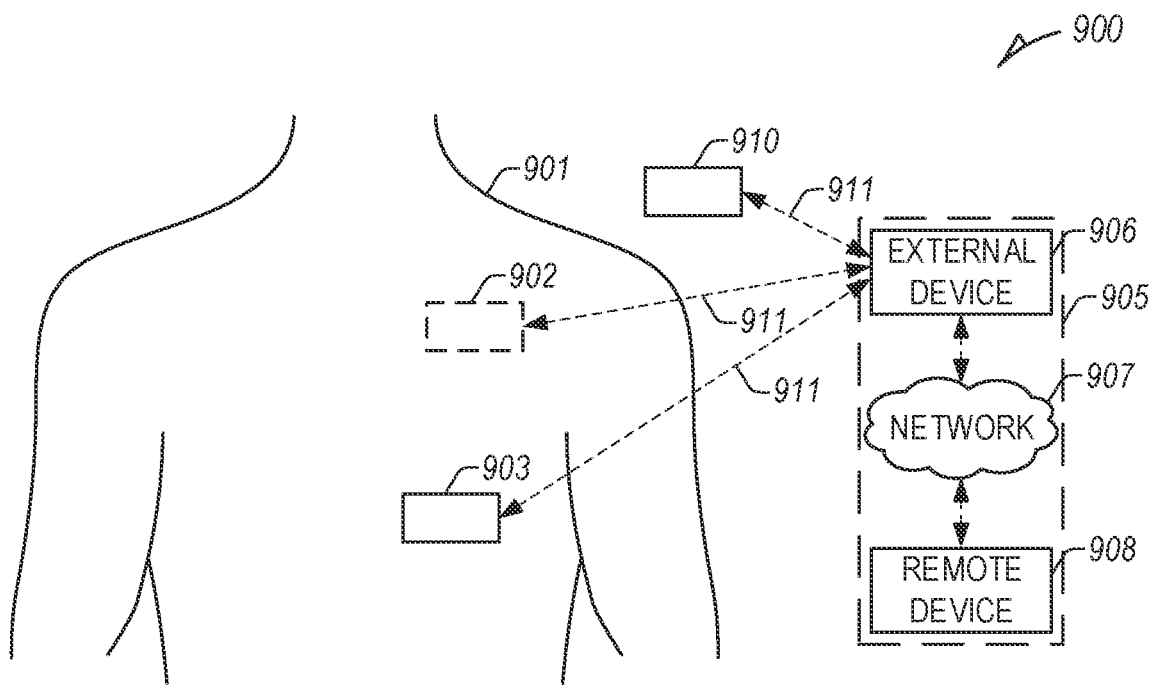
FIG. 9 illustrates an example patient management system.

FIG. 9 illustrates an example patient management system 900 and portions of an environment in which the system 900 may operate. The patient management system 900 can perform a range of activities, including remote patient monitoring and diagnosis of a disease condition. Such activities can be performed proximal to a patient 901, such as in a patient home or office, through a centralized server, such as in a hospital, clinic, or physician office, or through a remote workstation, such as a secure wireless mobile computing device.

The patient management system 900 can include one or more AMDs, an external system 905, and a communication link 911 providing for communication between the one or more AMDs and the external system 905. The one or more AMDs can include an implantable medical device (IMD) 902, a wearable medical device 903, or one or more other implantable, leadless, subcutaneous, external, wearable, or AMDs configured to monitor, sense, or detect information from, determine physiologic information about, or provide one or more therapies to treat various conditions of the patient 901, such as one or more cardiac or non-cardiac conditions (e.g., dehydration, etc.).

In an example, the IMD 902 can include one or more traditional cardiac rhythm management (CRM) devices, such as a pacemaker or defibrillator, implanted in a chest of a patient, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the patient 901. In another example, the IMD 902 can include a monitor implanted, for example, subcutaneously in the chest of patient 901.

The IMD 902 can include an assessment circuit configured to detect or determine specific physiologic information of the patient 901, or to determine one or more conditions or provide information or an alert to a user, such as the patient 901 (e.g., a patient), a clinician, or one or more other caregivers or processes. The IMD 902 can alternatively or additionally be configured as a therapeutic device configured to treat one or more medical conditions of the patient 901. The therapy can be delivered to the patient 901 via the lead system and associated electrodes or using one or more other delivery mechanisms. The therapy can include delivery of one or more drugs to the patient 901 using the IMD 902 or one or more of the other AMDs. In some examples, therapy can include CRT for rectifying dyssynchrony and improving cardiac function in CHF patients. In other examples, the IMD 902 can include a drug delivery system, such as a drug infusion pump to deliver drugs to the patient for managing arrhythmias or complications from arrhythmias, hypertension, or one or more other physiologic conditions.

The wearable medical device 903 can include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.). The wearable medical device 903 can include an optical sensor configured to detect a PPG signal on a wrist, finger, or other location on the patient 901. In other examples, the wearable medical device 903 can include an acoustic sensor or accelerometer to detect acoustic information (e.g., heart sounds) or the sound or vibration of blood flow, an impedance sensor to detect impedance variations associated with changes in blood flow or volume, a temperature sensor to detect temperature variation associated with blood flow, a laser Doppler vibrometer or other pressure, strain, or physical sensor to detect physical variations associated with blood flow, etc.

The patient management system 900 can include, among other things, a respiration sensor configured to receive respiration information (e.g., a respiration rate, a respiration volume (a minute volume (MV), a tidal volume (TV), etc.), etc.), a heart sound sensor configured to receive heart sound information, a thoracic impedance sensor configured to receive impedance information, a cardiac sensor configured to receive cardiac electrical information, an activity sensor configured to receive information about a physical motion (e.g., activity, posture, etc.), a plethysmography sensor, or one or more other sensors configured to receive physiologic information of the patient 901.

The external system 905 can include a dedicated hardware/software system, such as a programmer, a remote server-based patient management system, or alternatively a system defined predominantly by software running on a standard personal computer. The external system 905 can manage the patient 901 through the IMD 902 or one or more other AMDs connected to the external system 905 via a communication link 911. In other examples, the IMD 902 can be connected to the wearable device 903, or the wearable device 903 can be connected to the external system 905, via the communication link 911. This can include, for example, programming the IMD 902 to perform one or more of acquiring physiologic data, performing at least one self-diagnostic test (such as for a device operational status), analyzing the physiologic data to detect a cardiac arrhythmia, or optionally delivering or adjusting a therapy to the patient 901. Additionally, the external system 905 can send information to, or receive information from, the IMD 902 or the wearable device 903 via the communication link 911. Examples of the information can include real-time or stored physiologic data from the patient 901, diagnostic data, such as detection of patient hydration status, hospitalizations, responses to therapies delivered to the patient 901, or device operational status of the IMD 902 or the wearable device 903 (e.g., battery status, lead impedance, etc.). The communication link 911 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

By way of example and not limitation, the external system 905 can include an external device 906 in proximity of the one or more AMDs, and a remote device 908 in a location relatively distant from the one or more AMDs, in communication with the external device 906 via a communication network 907. Examples of the external device 906 can include a medical device programmer.

The remote device 908 can be configured to evaluate collected patient or patient information and provide alert notifications, among other possible functions. In an example, the remote device 908 can include a centralized server acting as a central hub for collected data storage and analysis. The server can be configured as a uni-, multi-, or distributed computing and processing system. The remote device 908 can receive data from multiple patients. The data can be collected by the one or more AMDs, among other data acquisition sensors or devices associated with the patient 901. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more AMDs, such as the IMD. By way of example, alert notifications can include a Web page update, phone or pager call, E-mail, SMS, text or "Instant" message, as well as a message to the patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiologic data associated with the detected medical event to physiologic data associated with the historical alerts.

The remote device 908 may additionally include one or more locally configured clients or remote clients securely connected over the communication network 907 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 908, including the server and the interconnected clients, may also execute a follow-up scheme by sending follow-up requests to the one or more AMDs, or by sending a message or other communication to the patient 901 (e.g., the patient), clinician or authorized third party as a compliance notification.

The communication network 907 can provide wired or wireless interconnectivity. In an example, the communication network 907 can be based on the Transmission Control Protocol/Internet Protocol (TCP/IP) network communication specification, although other types or combinations of networking implementations are possible. Similarly, other network topologies and arrangements are possible.

One or more of the external device 906 or the remote device 908 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 906 or the remote device 908 can include a respective display unit for displaying the physiologic or functional signals, or alerts, alarms, emergency calls, or other forms of warnings to signal the detection of arrhythmias. In some examples, the external system 905 can include an external data processor configured to analyze the physiologic or functional signals received by the one or more AMDs, and to confirm or reject the detection of arrhythmias. Computationally intensive algorithms, such as machine-learning algorithms, can be implemented in the external data processor to process the data retrospectively to detect cardia arrhythmias.

Portions of the one or more AMDs or the external system 905 can be implemented using hardware, software, firmware, or combinations thereof. Portions of the one or more AMDs or the external system 905 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" can include electronic circuits configured to receive information and provide an electronic output representative of such received information.

The patient management system 900 can include a therapy device 910, such as a respiratory therapy device (e.g. continuous positive airway pressure device or nebulizer device, etc.) or a drug delivery device configured to provide therapy or therapy information (e.g., dosage information, etc.) to the patient 901, such as using information from one or more of the AMDs. In other examples, one or more of the AMDs can be configured to provide therapy or therapy information to the patient 901. The therapy device 910 can be configured to send information to or receive information from one or more of the AMDs or the external system 905 using the communication link 911. In an example, the one or more AMDs, the external device 906, or the remote device 908 can be configured to control one or more parameters of the therapy device 910.

The external system 905 can allow for programming the one or more AMDs and can receives information about one or more signals acquired by the one or more AMDs, such as can be received via a communication link 911. The external system 905 can include a local external IMD programmer. The external system 905 can include a remote patient management system that can monitor patient status or adjust one or more therapies such as from a remote location.

The assessment circuit may be implemented at the external system 905, which can be configured to perform HF risk stratification such as using data extracted from the one or more AMDs or data stored in a memory within the external system 905. Portions of patient chronic condition-based HF or other assessment circuit may be distributed between the one or more AMDs and the external system 905.

Figure 10:
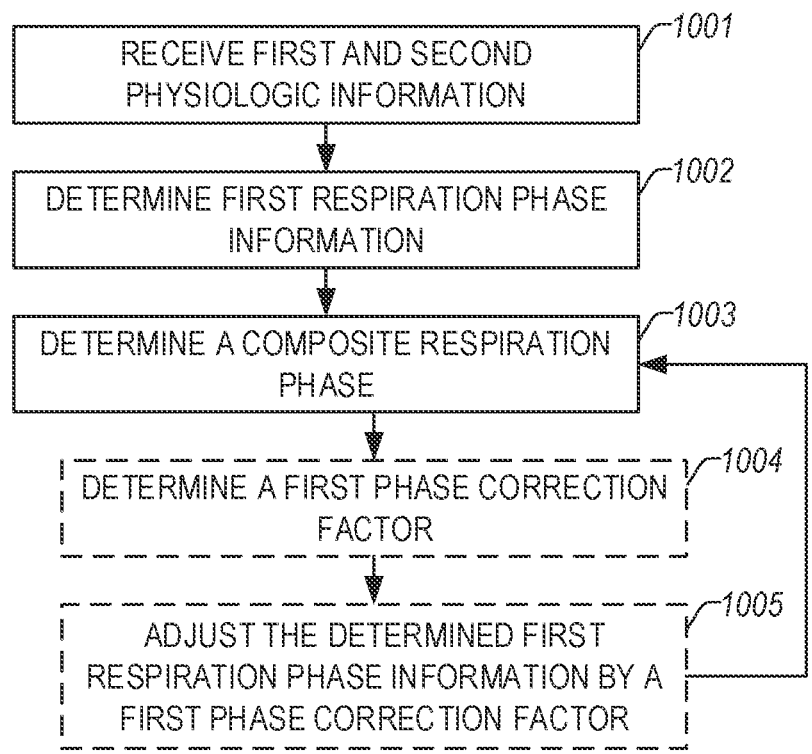
FIGS. 10 and 11 illustrate example methods to determine a composite respiration phase of a patient.

FIG. 10 illustrates an example method 1000 to determine a composite respiration phase of a patient using received first and second physiologic information of the patient. At 1001, first and second physiologic information can be received, such as at a signal receiver circuit of a system, such as a medical-device system. The first and second physiologic information can include indirect respiration measurements, or including physiologic information having a respiration component.

One or both of the first and second physiologic information can include physiologic signals having a respiration component (e.g., having a component cyclic with patient respiration, etc.), such as one or more of an electrocardiogram (ECG) signal, an accelerometer signal, or a photoplethysmography (PPG) signal, etc. In other examples, additional physiologic information can be received.

The first physiologic information can be different than the second physiologic information. The first physiologic information can include information from a first physiologic signal over a first period, and the second physiologic information can include information from a second physiologic signal over a second period. In certain examples, each of the first and second periods can include at least a portion of a respiratory cycle of the patient. In other examples, each of the first and second periods can include at least one full respiratory cycle of the patient. In an example, the second period can at least partially overlap the first period.

At 1002, first respiration phase information of the first physiologic information can be determined, such as using an assessment circuit. The first respiration phase information can include information indicative of inspiration and expiration of the patient, including, for example, transitions between inspiration and expiration of multiple respiration phases (e.g., sequential respiration phases).

At 1003, a composite respiration phase of the patient, indicative of patient inspiration and expiration, can be determined using the determined first respiration phase information and the received second physiologic information, such as using the assessment circuit. Certain physiologic information is indicative of one of peak inspiration or expiration of the patient, but less indicative of the other, or less indicative of specific transitions from inspiration to expiration or from expiration to inspiration. Accordingly, to increase the sensitivity or accuracy of specific respiration phase detection, including the transitions between inspiration and expiration, respectively, composite respiration information from separate sensors or different received physiologic information can be used. The composite respiration phase of the patient can be indicative of patient respiration phase, more consistent and accurate with that determined using a direct airflow measurement than separate indirect measurements, in certain examples, without the lead or lag associated with other indirect respiration measurements.

In an example, the second physiologic information can be cyclic with patient respiration or otherwise indicative of a specific phase or portion of the patient respiration signal. In an example, second respiration phase information of the second physiologic information can be determined, such as using the assessment circuit, and can include information indicative of inspiration and expiration of the patient such as described above with respect to the first respiration phase information. In an example, the composite respiration phase can be determined using the determined first respiration phase information and the determined second respiration phase information.

At 1004, a first phase correction factor can be determined for the first respiration phase information using the second physiologic information, including, in certain examples, determined second respiration phase information. In an example, the composite respiration phase of the patient can be determined using the determined first respiration phase information and the determined first phase correction factor. At 1005, the determined first respiration information can be adjusted by the first phase correction factor.

Figure 11:
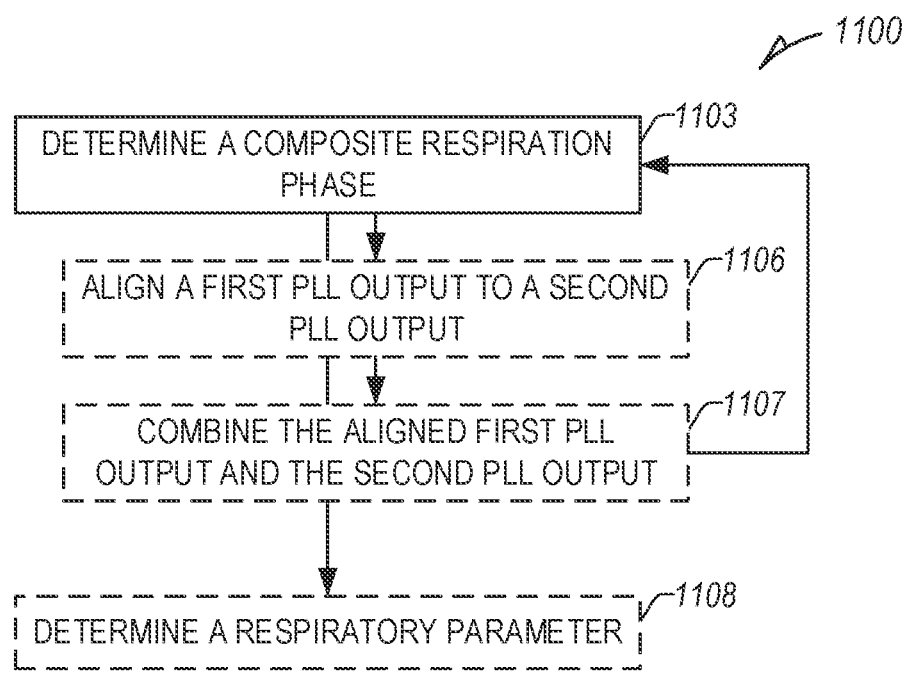

FIG. 11 illustrates an example method 1100 including, at 1103, determining, using an assessment circuit, a composite respiration phase of the patient using determined first respiration phase information and received second physiologic information. In an example, the assessment circuit can include one or more phase lock loop (PLL) circuits. In an example, a first PLL circuit can receive first physiologic information and provide a first PLL output, and a second PLL circuit can receive second physiologic information and provide a second PLL output.

At 1106, the first PLL output can be aligned to a second PLL output or other physiologic information of the patient having a respiratory component cyclic with respiration. At 1107, the aligned first PLL output and the second PLL output can be combined, such as using an adder circuit or other component of the assessment circuit, etc.

At 1108, a respiratory parameter of the patient can be determined using the determined composite respiration phase of the patient, in certain examples, in addition to one or more other physiologic information from the patient. The determined respiratory parameter can include one or more of the I/E ratio, FEV1, FVC, RR, TV, respiratory sounds, etc. In other examples, the determined composite respiration phase of the patient can be used to determine one or more other physiologic parameters, including cardiac parameters, such as murmurs, etc.

Figure 12:
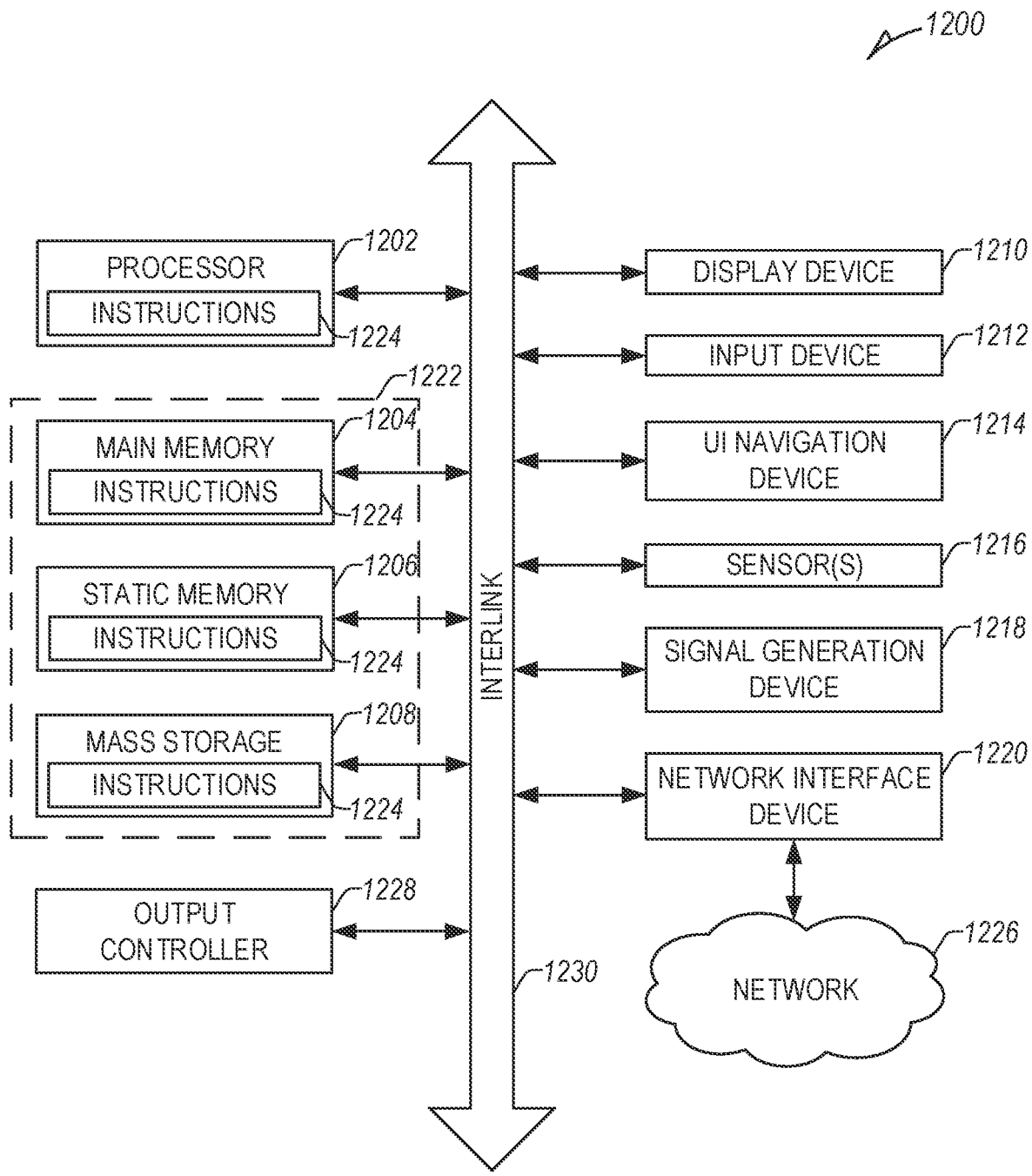
FIG. 12 illustrates a block diagram of an example machine upon which any one or more of the techniques (e.g., methodologies) discussed herein may perform.

FIG. 12 illustrates a block diagram of an example machine 1200 upon which any one or more of the techniques (e.g., methodologies) discussed herein may perform. Portions of this description may apply to the computing framework of one or more of the medical devices described herein, such as the IMD, the external programmer, etc. Further, as described herein with respect to medical device components, systems, or machines, such may require regulatory-compliance not capable by generic computers, components, or machinery.

Examples, as described herein, may include, or may operate by, logic or a number of components, or mechanisms in the machine 1200. Circuitry (e.g., processing circuitry, an assessment circuit, etc.) is a collection of circuits implemented in tangible entities of the machine 1200 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 1200 follow.

In alternative embodiments, the machine 1200 may operate as a standalone device or may be connected (e.g., networked) to other machines. In a networked deployment, the machine 1200 may operate in the capacity of a server machine, a client machine, or both in server-client network environments. In an example, the machine 1200 may act as a peer machine in peer-to-peer (P2P) (or other distributed) network environment. The machine 1200 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 1200 may include a hardware processor 1202 (e.g., a central processing unit (CPU), a graphics processing unit (GPU), a hardware processor core, or any combination thereof), a main memory 1204, a static memory (e.g., memory or storage for firmware, microcode, a basic-input-output (BIOS), unified extensible firmware interface (UEFI), etc.) 1206, and mass storage 1208 (e.g., hard drive, tape drive, flash storage, or other block devices) some or all of which may communicate with each other via an interlink (e.g., bus) 1230. The machine 1200 may further include a display unit 1210, an alphanumeric input device 1212 (e.g., a keyboard), and a user interface (UI) navigation device 1214 (e.g., a mouse). In an example, the display unit 1210, input device 1212, and UI navigation device 1214 may be a touch screen display. The machine 1200 may additionally include a signal generation device 1218 (e.g., a speaker), a network interface device 1220, and one or more sensors 1216, such as a global positioning system (GPS) sensor, compass, accelerometer, or one or more other sensors. The machine 1200 may include an output controller 1228, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 1202, the main memory 1204, the static memory 1206, or the mass storage 1208 may be, or include, a machine-readable medium 1222 on which is stored one or more sets of data structures or instructions 1224 (e.g., software) embodying or utilized by any one or more of the techniques or functions described herein. The instructions 1224 may also reside, completely or at least partially, within any of registers of the processor 1202, the main memory 1204, the static memory 1206, or the mass storage 1208 during execution thereof by the machine 1200. In an example, one or any combination of the hardware processor 1202, the main memory 1204, the static memory 1206, or the mass storage 1208 may constitute the machine-readable medium 1222. While the machine-readable medium 1222 is illustrated as a single medium, the term "machine-readable medium" may include a single medium or multiple media (e.g., a centralized or distributed database, and/or associated caches and servers) configured to store the one or more instructions 1224.

The term "machine-readable medium" may include any medium that is capable of storing, encoding, or carrying instructions for execution by the machine 1200 and that cause the machine 1200 to perform any one or more of the techniques of the present disclosure, or that is capable of storing, encoding, or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1224 may be further transmitted or received over a communications network 1226 using a transmission medium via the network interface device 1220 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.12 family of standards known as Wi-Fi®, IEEE 802.16 family of standards known as WiMax®), IEEE 802.15.4 family of standards, peer-to-peer (P2P) networks, among others. In an example, the network interface device 1220 may include one or more physical jacks (e.g., Ethernet, coaxial, or phone jacks) or one or more antennas to connect to the communications network 1226. In an example, the network interface device 1220 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 1200, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system, comprising:
    a signal receiver circuit configured to receive first and second physiologic information of a patient, the second physiologic information different than the first physiologic information, the first physiologic information cyclic with patient respiration; and
    an assessment circuit configured to:
        determine first respiration phase information of the first physiologic information, the first respiration phase information indicative of inspiration and expiration of the patient;
        determine a first phase correction factor for the determined first respiration phase information using the second physiologic information, wherein the first phase correction factor is configured to align the first respiration phase information with patient airflow;
        determine a composite respiration phase of the patient using the determined first respiration phase information and the determined first phase correction factor; and
    output a composite respiration signal having the determined composite respiration phase.

2. The system of claim 1, wherein the second physiologic information is cyclic with patient respiration.

3. The system of claim 2, wherein the assessment circuit is configured to:
    determine second respiration phase information of the second physiologic information, the second respiration phase information indicative of inspiration and expiration of the patient; and
    determine the composite respiration phase of the patient using the determined first and second respiratory phase information.

4. The system of claim 3, wherein the assessment circuit is configured to:
    determine a first phase correction factor for the determined first respiration phase information using the determined second respiratory phase information; and
    determine the composite respiration phase of the patient using the determined first respiration phase information and the determined first phase correction factor.

5. The system of claim 4, wherein, to determine the composite respiration phase of the patient, the assessment circuit is configured to adjust the determined first respiration phase information by the first phase correction factor.

6. The system of claim 4, wherein the assessment circuit comprises:
    a first phase lock loop (PLL) circuit configured to receive the first physiologic information and provide a first PLL output; and
    a second PLL circuit configured to receive the second physiologic information and provide a second PLL output,
    wherein the assessment circuit is configured to align the first PLL output to the second PLL output using the determined first phase correction factor, and to combine the aligned first PLL output and the second PLL output, and
    wherein the assessment circuit is configured to determine the composite respiration phase of the patient using the combined aligned first PLL output and the second PLL output.

7. The system of claim 3, wherein the assessment circuit is configured to determine a change in patient status, to detect a physiological condition of the patient, or to determine a patient therapy parameter using a determined change in the first respiration phase information over time relative to the second respiration phase information over time or the determined composite respiration phase of the patient over time.

8. The system of claim 1, wherein the first and second physiologic information comprise different types of information comprising two or more of electrocardiogram information of the patient, accelerometer information of the patient, or blood flow information of the patient.

9. The system of claim 8, wherein the first physiologic information comprises information from a first physiologic signal over a first period, the second physiologic information comprises information from a second physiologic signal different than the first physiologic signal over a second period, wherein the first and second periods at least partially overlap,
wherein electrocardiogram information of the patient comprises R-wave amplitude information of the patient or electrocardiogram heart rate information of the patient, and
wherein accelerometer information of the patient comprises accelerometer information indicative of patient chest motion.

10. The system of claim 1, wherein the assessment circuit is configured to determine a respiratory parameter using the composite respiration phase, and
wherein the respiratory parameter comprises at least one of an inspiration to expiration (I/E) ratio or respiratory sounds.

11. The system of claim 1, wherein patient airflow includes positive and negative patient oronasal airflow, and wherein the first and second physiologic information are separate from patient oronasal airflow.

12. The system of claim 1, wherein the first physiological information includes a first non-sinusoidal signal cyclic with patient respiration, and
wherein the assessment circuit is configured to determine and output the composite respiration signal, wherein the composite respiration signal includes a sinusoidal signal having the determined composite respiration phase.

13. A method, comprising:
receiving, at a signal receiver circuit, first and second physiologic information of a patient, the second physiologic information different than the first physiologic information, the first physiologic information cyclic with patient respiration;
determining, using an assessment circuit, first respiration phase information of the first physiologic information, the first respiration phase information indicative of inspiration and expiration of the patient;
determining, using the assessment circuit, a first phase correction factor for the determined first respiration phase information using the second physiologic information, wherein the first phase correction factor is configured to align the first respiration phase information with patient airflow;
determining, using the assessment circuit, a composite respiration phase of the patient using the determined first respiration phase information and the determined first phase correction factor; and
outputting, using the assessment circuit, a composite respiration signal having the determined composite respiration phase.

14. The method of claim 13, comprising:
determining, using the assessment circuit, second respiration phase information of the second physiologic information, the second physiologic information cyclic with patient respiration, the second respiration phase information indicative of inspiration and expiration of the patient; and determining, using the assessment circuit, a first phase correction factor for the determined first respiration phase information using the determined second respiratory phase information,
wherein determining the composite respiration phase of the patient comprises using the determined first respiration phase information and the determined first phase correction factor.

15. The method of claim 14, wherein, to determine the composite respiration phase of the patient, the assessment circuit is configured to adjust the determined first respiration phase information by the first phase correction factor.

16. The method of claim 14, wherein determining first respiration phase information of the first physiologic information comprises:
receiving the first physiologic information using a first phase lock loop (PLL) circuit and providing a first PLL output; and
receiving the second physiologic information using a second PLL circuit and providing a second PLL output, and
wherein determining the composite respiration phase of the patient comprises:
aligning the first PLL output to the second PLL output using the determined first phase correction factor; and
combining the aligned first PLL output and the second PLL output.

17. The method of claim 13, wherein the first and second physiologic information comprise different types of information comprising two or more of electrocardiogram information of the patient, accelerometer information of the patient, or blood flow information of the patient,
wherein the first physiologic information comprises information from a first physiologic signal over a first period, the second physiologic information comprises information from a second physiologic signal different than the first physiologic signal over a second period, wherein the first and second periods at least partially overlap,
wherein electrocardiogram information of the patient comprises R-wave amplitude information of the patient or electrocardiogram heart rate information of the patient, and
wherein accelerometer information of the patient comprises accelerometer information indicative of patient chest motion, wherein the method comprises:
determining, using the assessment circuit, a respiratory parameter using the composite respiration phase,
wherein the respiratory parameter comprises at least one of an inspiration to expiration (I/E) ratio or respiratory sounds.

18. At least one non-transitory machine-readable medium comprising instructions that, when performed by a medical device, cause the medical device to:
receive first and second physiologic information of a patient, the second physiologic information different than the first physiologic information, the first physiologic information cyclic with patient respiration;
determine first respiration phase information of the first physiologic information, the first respiration phase information indicative of inspiration and expiration of the patient;
determining a first phase correction factor for the determined first respiration phase information using the second physiologic information, wherein the first phase correction factor is configured to align the first respiration phase information with patient airflow;

determine a composite respiration phase of the patient using the determined first respiration phase information and the determined first phase correction factor; and outputting a composite respiration signal having the determined composite respiration phase.

19. The at least one non-transitory machine-readable medium of claim 18, wherein the instructions, when performed by the medical device, cause the medical device to:

determine second respiration phase information of the second physiologic information, the second physiologic information cyclic with patient respiration, the second respiration phase information indicative of inspiration and expiration of the patient; and determine a first phase correction factor for the determined first respiration phase information using the determined second respiratory phase information, wherein to determine the composite respiration phase of the patient comprises using the determined first respiration phase information and the determined first phase correction factor.

* * * * *